United States Patent [19]

Tong

[11] 3,987,044
[45] Oct. 19, 1976

[54] SEPARATION OF 2,3-DIAMINO-DIHALOPYRAZINES FROM MIXTURES AS NOVEL ASSOCIATION PRODUCTS WITH CERTAIN KETONES

[75] Inventor: Yulan C. Tong, Walnut Creek, Calif.

[73] Assignee: The Dow Chemical Company, Midland, Mich.

[22] Filed: Aug. 18, 1975

[21] Appl. No.: 605,682

[52] U.S. Cl. .......................... 260/250 BN; 424/250
[51] Int. Cl.$^2$ ....................................... C07D 241/16
[58] Field of Search ............................. 260/250 BN

[56] References Cited
OTHER PUBLICATIONS
G. Palamidessi et al., Chemical Abstracts, vol. 66, 37,886g, (1967).

Primary Examiner—Nicholas S. Rizzo
Assistant Examiner—Jose Tovar
Attorney, Agent, or Firm—Robert R. Stringham

[57] ABSTRACT

Insoluble association products are formed when solid 2,3-diamino-5,6-dihalopyrazines are contacted with liquid ketones of the structure $R^1—CH_2—CO—CH_2—R^2$, wherein $R^1$ and $R^2$ are both H or together constitute a polymethylene chain of from 2 to 4 carbons. The isomeric 2,6-diamino-dihalopyrazines dissolve in the ketones. Thus, mixtures of the solid 2,3-diamino-dihalopyrazines with their isomers and/or other ketone-soluble materials can be resolved by contacting the mixtures with ketones of the preceding structure and separating the resultant solid and liquid phases. The association products constitute a novel composition of matter.

10 Claims, No Drawings

SEPARATION OF 2,3-DIAMINO-DIHALOPYRAZINES FROM MIXTURES AS NOVEL ASSOCIATION PRODUCTS WITH CERTAIN KETONES

BACKGROUND OF THE INVENTION 2,3-Diamino-5,6-dihalopyrazines, in which halo is Br, Cl or F, are intermediates for the preparation of herbicides and antimicrobials. U.S. Pat. No. 3,822,261 discloses the preparation of herbicidal imidazopyrazines such as

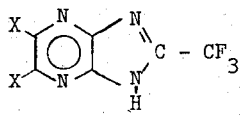

from the corresponding pyrazine compounds

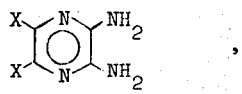

X being Br, Cl or F. U.S. Pat. No. 3,850,929 similarly discloses the preparation of microbicidal thiadiazolopyrazines of the structure

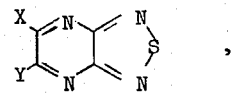

in which X and Y are Br or Cl.

The 2,3-diamino-5,6-dihalopyrazine intermediates utilized in the preceding patents can be prepared by reacting corresponding tetrahalopyrazines with ammonium hydroxide, according to the procedure of G. Palamidessi and F. Luini, Farmaco. Gd. Sci., 21, 811 (1966); Chemical Abstracts, 66, 37886g (1967). However, the 2,6-diamino-dihalo isomers are co-produced with the desired intermediates (except when tetrafluoropyrazine is the starting material). Palamidessi and Luini disclose no method of separating the isomers, as such, from each other and ordinary separatory procedures, such as fractional crystallization are generally not effective for this purpose. In those instances where the mixed isomers cannot be employed as such (as by selective reaction or conversion to more readily separated isomeric products), a convenient method of separation is highly desirable.

OBJECTS OF THE INVENTION

The primary object of the present invention is to provide a method of separating 2,3-diamino- and 2,6-diaminodihalopyrazines.

An additional object is to provide a method of purifying solid 2,3-diamino-dihalopyrazines, i.e., of separating such compounds from ketone-soluble materials in general, including non-isomeric diamino-dihalopyrazines.

A further object is to provide, as novel compositions of matter, solid association products of 2,3-diamino-dihalopyrazines with ketones of the structure $R^1$—$CH_2CO$—$CH_2$—$R^2$, wherein $R^1$ and $R^2$ are both H or together constitute a polymethylene chain of from 2 to 4 carbons.

SUMMARY OF THE INVENTION

It has now been discovered that the foregoing objects are attainable by contacting mixtures comprising solid 2,3-diamino-dihalopyrazines and ketone-soluble materials with liquid ketones as above defined and separating the resultant solid and liquid phases.

More precisely, the method of the present invention is definable as:

A process for separating a solid, diamino-dihalopyrazine from a mixture thereof with a ketone-soluble material, said pyrazine having the structure

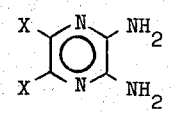

wherein both X's are Br, Cl or F or one is Cl and the other is Br or F,
said ketone being a liquid and having the structure $R^1$—$CH_2CO$—$CH_2$—$R^2$, in which $R^1$ and $R^2$ are both H or together constitute a polymethylene chain of from 2 to 4 carbons,
said process comprising:
1. contacting said mixture with said ketone in an amount sufficient to form a liquid solution of said material and to convert said pyrazine to a solid ketone association product, and
2. separating said product from said solution.

In one embodiment of the preceding process invention, the ketone-soluble material is a dihalo-diaminopyrazine of the structure

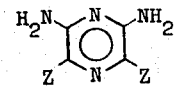

wherein Z is Br or Cl, independently in each occurrence.

In another embodiment, the process of the present invention comprises the additional step of isolating said pyrazine by decomposing the separated association product.

The present invention also embraces the solid association products formed by contacting said 2,3-diamino-5,6-dihalopyrazines with said ketones.

DETAILED DESCRIPTION OF THE INVENTION

Suitable mixtures for the practice of the present invention are mixtures of a solid 2,3-diamino-5,6-dihalopyrazine with any other material which is soluble in a ketone as above defined. Such soluble materials may be present in the mixture as solids or liquids or as absorbed or adsorbed gases. Mixtures in which the diamino-dihalo pyrazine particles are encapsulated in or completely coated with a material which is not pervious to the ketone cannot be converted to an association product with the ketone and are of course excluded from the practice of the invention. However, the latter type of mixtures will ordinarily not be encountered.

The 2,3-diamino-dihalopyrazine may be included in or constitute a solid phase which is covered by or suspended in a ketone-miscible liquid from which it is not readily or efficiently separable. In the latter case, the liquid may simply be a saturated solution of the pyrazine compound in a ketone-miscible solvent. The ketone associable pyrazine compound present as a solute will generally not be precipitated by mixing the saturated solution with the ketone and the undissolved pyrazine compound will be converted into the association product without dissolving.

The most important application of the invention is in the separation of 2,3-diamino-dihalopyrazines from 2,6-diamino-dihalopyrazines, particularly when the halo substituents are the same therein, i.e., when the compounds to be separated are isomers of each other. In this application, the mixture to be resolved will ordinarily consist essentially only of solids.

In general, any 2,3-diamino-dihalopyrazine

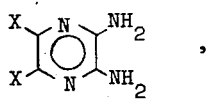

in which both X's are Br, Cl or F or one X is Cl and the other is Br or F, can be separated as an insoluble ketone-association product from any 2,6-diamino-dihalopyrazine

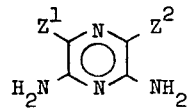

in which $Z^1$ and $Z^2$ are independently Br or Cl, by contacting a mixture of the 2,3- and 2,6-diamino-dihalo compounds with acetone, cyclopentanone, cyclohexanone, cycloheptanone or mixtures thereof.

Suitable ketones for the present process are acetone, cyclopentanone, cyclohexanone, cycloheptanone and mixtures thereof. Surprisingly, methyl ethyl ketone was found unsuitable for the separation of 2,3-diamino-5,6-dihalopyrazines from their 2,6-diaminodihalo isomers. Selective formation of an association product with the 2,3-diamino compounds apparently is dependent on the structural features common to the preceding group of ketones.

It is desirable but not indispensable that the ketone employed be highly pure. Incidental impurities and ketones or other solvents which cannot be used in place of the ketones specified for the practice of the present process may be present in minor amounts, up to a maximum of about 10 weight percent. Thus, the ketone used does not have to be anhydrous and ordinary drum stock ketones, such as solvent grade acetone, will usually be quite satisfactory.

The amount of ketone employed must be at least sufficient to dissolve the other materials from which the 2,3-diamino-dihalopyrazine is to be separated and to convert the latter compound to the association product. Desirably, however, more than the minimum amount of the ketone will ordinarily be used to facilitate stirring and handling. Although the association product will have some solubility in the ketone, significant losses do not result from washing the product with at least enough fresh ketone to essentially free the association product of the other components of the original mixture. At ordinary temperatures, relatively large amounts of ketone may be employed in the separation without experiencing excessive solubility losses of the association product.

However, at higher temperatures (up to the boiling point of the ketone(s)), solubility losses will be greater unless the amount of ketone used is not large. In any case, the amount of ketone used must not be so great but what some of the 2,3-diamino-dihalopyrazine will remain undissolved at the contemplated temperature of operation.

Suitable temperatures for the practice of the present invention range from such low temperatures that some of the "ketone-soluble" material actually remains undissolved up to temperatures such that a substantial proportion of the 2,3-diamino-dihalopyrazine dissolves. As a general rule, temperatures above the boiling point of acetone (~56° C.) will not be employed, even with higher boiling ketones (or mixtures of same). Ordinary ambient temperatures are most convenient and will usually be preferred.

The present process can readily be carried out at atmospheric or superatmospheric pressures but sub-atmospheric pressures will generally not be appropriate. Operation at ordinary ambient pressures is most convenient and is preferred.

The contact time required to effect a desired degree of resolution of a given mixture will depend primarily on the rate at which 2,3-diamino-dihalopyrazine particles in the mixture are exposed to contact with the ketone used, as by leaching out of soluble materials, such as 2,6-diamino-dihalopyrazines, which may be present as coatings on or otherwise occlude the surfaces of said particles. Relatively brief contact periods, such as from a few minutes (with good agitation) to a few hours (with poor agitation) are generally adequate. Of course, super-ambient temperatures may also be resorted to in order to decrease the contact time required. In any case, the minimum time to effect any desired degree of resolution of any particular mixture at any selected temperature can readily be determined by routine testing.

It is not to be construed from the foregoing teachings that the present invention is predicated on specific values of such operating parameters as the amount or purity of the ketone employed or temperature, pressure or contact time. It is the formation of the association product, when the surfaces of solid particles of 2,3-diamino-dihalopyrazines are contacted with liquid ketones of a certain type, that constitutes a unique phenomenon of which advantage can be taken to resolve mixtures of the latter pyrazines with other materials.

GENERAL PROCEDURE

The mixture to be resolved is intimately contacted with the ketone, as by stirring a powdered mixture of solids with enough of the ketone to give a readily stirred dispersion. The solid and liquid phases are then separated by conventional procedures, such as settling and decanting, filtration or centrifuging. The separated solid is washed with fresh ketone and may be further washed with a more readily volatilized liquid which is a solvent for the ketone but not for the association product (or at least not for the 2,3-diamino-dihalo component thereof). The association product may then be utilized as such, as a 2,3-diamino-dihalopyrazine source material, or may be freed of its ketone content, as by warming it under vacuum. If desired, the 2,3-diamino-dihalo pyrazine can be recrystallized from a suitable solvent. This can be done without first removing the ketone from the association product, which will be decomposed when it is taken up in solution.

The relative amounts of the 2,3- and 2,6-diamino-dihalopyrazine isomers and other materials in mixtures thereof can conveniently be estimated by TLC (thin layer chromatography). The separated isomers may be identified by such conventional methods as elemental, IR (infrared) and NMR (nuclear magnetic resonance) analyses, melting point, etc.

The relative retention factors for the 2,3- and 2,6-diaminodichloropyrazine isomers on alumina TLC plates with anhydrous ethanol are 0.67 and 0.54 respectively. Comparable differences are found for the corresponding dibromo isomer pair.

EXAMPLES

EXAMPLE 1

In the manner of Palamidessi and Luini (loc. cit.), 46.2 grams of tetrachloropyrazine was agitated with 400 ml. of c. $NH_4OH$ in a glass-lined bomb at 120° C. for 14 hours. Filtration of the cooled and depressurized reaction mixture and drying gave 30.7 grams (82% of theory for diamino-dichloropyrazines) of a yellow crystalline solid. An additional 1.1 grams of solid was obtained by evaporating down the filtrate and recrystallizing the resulting residue from ethanol. TLC of the first solid with anhyd. ethanol on alumina showed it to consist of three compounds and to be free of amino-trichloropyrazine. When 3 grams of the first solid was boiled with 20 ml. of acetone only part of it dissolved. The acetone insoluble portion was filtered out and an air dried sample analyzed by NMR. A methyl group signal was found at 2.03 ppm, indicating acetone retention. The following results were obtained upon vacuum drying the acetone-insoluble solid and subjecting it to elemental analysis:

|  | C | H | N |
|---|---|---|---|
| Calc. for $C_4H_4Cl_2N_4$ | 26.84 | 2.25 | 31.30 |
| Found | 26.9 | 2.4 | 30.9 |

The vacuum dried solid (total 1.3 grams) was acetone-free (by IR) and melted at 278° C. Evaporation of the acetone filtrate gave 0.7 grams of a crystalline material which differed from the insoluble solid by IR.

The acetone-free, acetone-insoluble solid was confirmed as the 2,3-diamino-dichloropyrazine isomer by virtue of the fact that it could be cyclized, by reaction with trifluoroacetic anhydride, as disclosed in U.S. Pat. No. 3,822,261, to 5,6-dichloro-2-trifluoromethyl-1-H-imidazo(4,5-b) pyrazine.

EXAMPLE 2

60.0 Grams of tetrachloropyrazine was agitated with 500 ml. of c. $NH_4OH$ in a glass-lined bomb at 120° C. for 4 hours. 40 Grams of a yellow crystalline solid (dry wt.; 81% of theory) was recovered from the cooled and depressurized reaction mixture by filtration. TLC of this solid showed the presence of a small amount of amino-trichloropyrazine. The solid was mixed with 400 ml. of acetone, heated to boiling and filtered. The filtrand was obtained as a powder in the amount of 25 grams (air dry wt.). This weight was reduced to 19.8 grams upon vacuum drying, a loss of ~21% (in comparison to a theoretical loss of 25% for a 1:1 association product of acetone with a diamino-dichloro-pyrazine). A total of 19.4 grams of acetone-soluble material, indicated by IR to be a mixture of predominantly 2,6- and/or 2,5-diamino-dichloropyrazine with a little 2,3-diamino-dichloropyrazine, was recovered in 2 fractions by evaporative concentration of the acetone filtrate. The predominant soluble isomer was subsequently identified as the 2,6-diamino-dichloro compound.

EXAMPLE 3

25 Grams of tetrabromopyrazine was agitated with 200 ml. of c. $NH_4OH$ in a glass-lined bomb for 14 hours at 120° C. The cooled and depressurized reaction mixture was filtered. After being washed with water and air dried, the filtrand consisted of 13 grams of a brown mixture of plate and needleform crystals. A mixture of the crystals with 50 ml. of acetone was heated to boiling and filtered. The weight of the acetone-insoluble filtrand was 9.0 grams after drying and 7.2 grams after drying in vacuo overnight (a 20% loss, as compared to a theoretical loss of ~18% for a 1:1 acetone association product with a diamino-dibromopyrazine). The acetone-free filtrand was taken up in hot ethanol, treated with decolorizing charcoal and cooled. A first crop of 4.9 grams of crystals was sampled for elemental analysis:

|  | C | H | N |
|---|---|---|---|
| Calc. for $C_4H_4Br_2N_4$ | 17.93 | 1.50 | 20.91 |
| Found | 18.1 | 1.5 | 21.1 |

Evaporation of the acetone filtrate and recrystallization of the resulting residue from ethanol gave 2 grams of an acetone soluble solid (m.p. 160°–5° C.(d)) which was also sampled for elemental analysis:

|  | C | H | N |
|---|---|---|---|
| Found | 18.3 | 1.5 | 20.6 |

TLC with ethanol on alumina shows the latter solid to consist of only one component and the acetone-insoluble solid to consist of the latter component in minor proportion and of a different component in major proportion. The insoluble solid was rewashed with acetone, refiltered and dried in vacuo to a weight of 3.4 grams. TLC then showed the minor component to have been removed (in the acetone wash).

The wash (acetone filtrate) was combined with the ethanolic mother liquor from recrystallization of the initially recovered acetone-soluble material. Upon evaporation to dryness and washing the residue with 40 ml. of acetone, 0.8 grams (vacuum dry weight) of undissolved material was recovered in the form of plate-like crystals. Evaporation of the wash and recrystallization of the residue from ethanol gave 1.6 grams of dissolved material as needleform crystals. TLC showed the latter, acetone-insoluble and -soluble components to be free of each other. The insoluble solid was combined with the acetone-washed, initially recovered acetone-insoluble solid; the melting point of the mixed solids was 252° C.

On the basis of IR comparison with the isomeric diamino-dichloropyrazines, the 2,3-diaminodibromopyrazine configuration was assigned to the plate-form, higher melting, acetone-insoluble isomer. The needle-form, lower melting, soluble isomer was identified as 2,6-diamino-dibromopyrazine. dibromopyrazine. The configuration of the insoluble isomer was confirmed by conversion of it to dibromo-imidazopyrazine compounds as disclosed in U.S. Pat. No. 3,822,261. The identification of the predominant soluble isomer as 2,6-diamino-dibromopyrazine was subsequently confirmed by conversion to a known, non-cyclized product.

EXAMPLE 4

In each of three tared, medium frit, sintered glass funnels was placed 5 grams of a mixture of 2,3- and 2,6-diamino-dichloropyrazines. 25 ml. of cyclopentanone, cyclohexanone and cycloheptanone was added to the first, second and third funnels respectively. The resulting mixtures were each stirred, covered and allowed to filter over a weekend. Each filtrand was washed with methylene chloride (60 ml) and air dried. The dry solids and filtrates were checked by TLC and showed very clean separations in each case. The weights of the filtrands, after drying in vacuo at 80° C., were as follows:

| Solvent | Weight of Solid |
|---|---|
| Cyclopentanone | 2.90 grams |
| Cyclohexanone | 2.35 |
| Cycloheptanone | 2.70 |

The cyclopentanone filtrate was evaporated and the residue washed twice with $CH_2Cl_2$ and filtered. 1.6 Grams of solid identified by IR as the 2,6-diamino-dichloro isomer was recovered.

The foregoing examples are illustrative only and are not to be considered as limiting the scope of present invention in any manner inconsistent with the following claims.

Diamino-dihalopyrazines in which the two halo moieties are different, i.e., are Br and Cl or F and Cl, may be prepared by ammonolysis of mixed tetrahalopyrazines, such as tribromo-chloropyrazine or trifluoro-chloropyrazine, which are preparable by exchange reactions of tetrachloro pyrazine with KBr or KF in known types of procedures. Also, bromide ion may be exchanged for a chlorine in diamino-dichloropyrazines by similar procedures. See U.S. Pat. No. 3,822,261.

Because the ketone components of the association products formed with the 2,3-diamino-dihalopyrazines are not strongly bound and are relatively volatile, it is difficult to isolate the association products as definite composition of matter. However, it is evident from the weight losses found upon vacuum drying of the air dried materials that definite products in which the ketone and pyrazine components are associated in a 1:1 mole ratio are formed. These constitute a novel and useful composition of matter which may be defined as:

a solid association product in a mole ratio of 1:1 between a 2,3-diamino-5,6-dihalopyrazine,

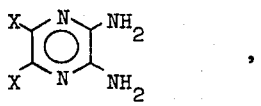

in which both X's are Br, Cl or F or one X is Cl and the other is Br or F, and a ketone $R^1$—$CH_2$—CO—CH$_2$—$R^2$, wherein $R^1$ and $R^2$ are both H or together constitute a polymethylene chain of 2 to 4 carbons, said product being characterized as having a low solubility in said ketone.

Preferably, X in the preceding association product is Br or Cl, independently, in each occurrence.

I claim:
1. A process for separating a solid, diamino-dihalopyrazine from a mixture thereof with a ketone-soluble material, said pyrazine having the structure

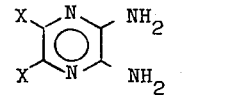

wherein both X's are Br, Cl or F or one is Cl and the other is Br or F,
said ketone being a liquid and having the structure $R^1$—$CH_2CO$—$CH_2$—$R^2$, in which $R^1$ and $R^2$ are both H or together constitute a polymethylene chain of from 2 to 4 carbons,
said process comprising:
1. contacting said mixture with said ketone in an amount sufficient to form a liquid solution of said material and to convert said pyrazine to a solid ketone association product, and
2. separating said product from said solution.

2. The process of claim 1 in which the ketone-soluble material is a dihalo-diaminopyrazine of the structure

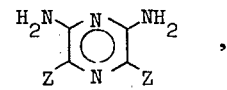

wherein Z is Br or Cl, independently in each occurrence.

3. The process of claim 1 which comprises the additional step of isolating said pyrazine by decomposing the separated association product.

4. The process of claim 1 in which said pyrazine is 2,3-diamino-5,6-dichloropyrazine or 2,3-diamino-5,6-dibromopyrazine.

5. The process of claim 4 in which the ketone-soluble material is the corresponding 2,6-diamino-3,5-dihalo isomer.

6. A solid association product in a mole ratio of 1:1 between a 2,3-diamino-5,6-dihalopyrazine,

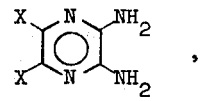

in which both X's are Br, Cl or F or one X is Cl and the other is Br or F, and a ketone $R^1$—$CH_2$—CO—$CH_2$—$R^2$, wherein $R^1$ and $R^2$ are both H or together constitute a polymethylene chain of 2 to 4 carbons, said product being characterized as having a low solubility in said ketone.

7. The product of claim 6 in which the ketone is acetone.

8. The product of claim 6 in which X is Br or Cl, independently, in each occurrence.

9. The product of claim 8 in which both X's are Br.

10. The product of claim 8 in which both X's are Cl.

* * * * *